US00PP28467P3

(12) United States Plant Patent
NeSmith

(10) Patent No.: US PP28,467 P3
(45) Date of Patent: Oct. 3, 2017

(54) DWARF HYBRID BLUEBERRY PLANT NAMED 'TO-1088'

(50) Latin Name: ***Vaccinium* spp. hybrid**
Varietal Denomination: TO-1088

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/756,563

(22) Filed: Sep. 17, 2015

(65) Prior Publication Data

US 2017/0086342 P1 Mar. 23, 2017

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

PUBLICATIONS

NeSmith. Ornamental Blueberry Variety Development at The University of Georgia A Progress Report for 2014 Small Fruit News vol. 15, No. 3 2015, retrieved on Nov. 16, 2016, retrieved from the Internet at <http://www.smallfruits.org/Newsletter/Vol15-Issue3.pdf> pp. 1-6.*

NeSmith. Ornamental Blueberry Variety Development at The University of Georgia A Progress Report for 2012, retrieved on Nov. 16, 2016, retrieved from the Internet at <http://www.smallfruits.org/blueberries/production/ornamentalreport2012.pdf> pp. 1-16.*

* cited by examiner

*Primary Examiner* — June Hwu
(74) *Attorney, Agent, or Firm* — Klarquist Sparkman, LLP

(57) ABSTRACT

A new variety of blueberry plant, named 'TO-1088', has berries that ripen around late May in southern Georgia and mid-late June in middle Georgia. The fruit of the new variety 'TO-1088' are dark, small, and firm, with a mildly tart flavor. The new variety 'TO-1088' is vigorous with an estimated chilling requirement of about 400 to 500 hours at or below approximately 7° C.

10 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TO-1088' is a dwarf hybrid blueberry plant that is a *Vaccinium* spp. hybrid.

Variety denomination: The new dwarf hybrid blueberry plant claimed is of the variety denominated 'TO-1088'.

BACKGROUND OF THE INVENTION

The present invention relates to the discovery of a new and distinct cultivar of dwarf hybrid blueberry plant botanically known as a hybrid of *Vaccinium corymbosum, Vaccinium darrowii* and *Vaccinium virgatum* and herein referred to as 'TO-1088', as herein described and illustrated.

The new blueberry plant variety 'TO-1088' was selected in Griffin, Ga. in 2007. The 'TO-1088' variety was first asexually propagated by softwood cuttings in Griffin, Ga. in 2007. The resulting propagated plants were planted in field trials in 2009. The new variety 'TO-1088' ripens around late May in southern Georgia. The fruit of the new variety 'TO-1088' are small and dark with favorable scar. The new variety 'TO-1088' has good yield and is vigorous with an estimated chilling requirement of about 400-500 hours at or below 7° C.

Pedigree and history: 'TO-1088' was selected in 2007 at the Georgia Experiment Station in Griffin, Ga., originating from an open pollinated cross of 'MS-840' (a non-patented breeding line) made by Dr. Scott NeSmith in 2007. 'MS-840' originated from a cross of 'Bluecrisp' (U.S. Plant Pat. No. 11,033)×'Magnolia' (a non-patented commercial variety). Both 'Bluecrisp' and 'Magnolia' are mostly *Vaccinium corymbosum*, but have *V. darrowii* and *V. virgatum* in their ancestry. Plants of this new variety have been tested in plantings at UGA Blueberry Research Farms in Alapaha and Griffin, Ga. since 2008. The selection was planted in ornamental trials at the Alapaha and Griffin, Ga. locations in 2011.

SUMMARY OF THE INVENTION

The new blueberry plant variety 'TO-1088' has not been observed under all possible environmental conditions. The phenotype may vary somewhat with variations in environment and cultural practices such as temperature and light intensity without, however, any variance in genotype.

The following traits have been repeatedly observed in the original plant and in asexually propagated plants of the new variety, propagated by softwood cuttings, and growing in Alapaha and Griffin Ga., and are determined to be the unique firmly fixed combination of characteristics of the new blueberry plant variety 'TO-1088':

1. Dwarf or compact plant;
2. Good crop load for a dwarf plant;
3. Favorable scar;
4. Small berry size.

The new 'TO-1088' variety is a dwarf plant in comparison to the non-dwarf parent 'MS-840'. Three to four year old 'MS-840' plants were typically 1.0 to 1.6 m tall. The new 'TO-1088' variety has smaller berries than the berries of the 'MS-840' variety. Typical berries of the 'MS-840' variety were typically from 1.3 to 1.6 grams. The parent plant 'M-840' is no longer available.

The new variety 'TO-1088' can be compared to the rabbiteye variety 'Alapaha' (the subject of U.S. Plant Pat. No. 16,266) and southern highbush blueberry variety 'Camellia' (the subject of U.S. Plant Pat. No. 18,151).

Comparison: The selection flowers and ripens in between 'Camellia' in the late Georgia southern highbush season and 'Alapaha' in the early rabbiteye season. 'TO-1088' has small, dark berries and very good crop load for a dwarf plant, but with a typical plant yield that is likely only 1.5 to 2.5 pounds per plant. 'Camellia' and 'Alapaha' plants growing in Alapaha and Griffin, Ga. typically yield 12 to 14 pounds of fruit per plant. 'TO-1088' plants are very compact compared to 'Alapaha' and 'Camellia', making 'TO-1088' ideal for container production. 'TO-1088' plants are more dwarf and compact and have smaller leaves and berries than either 'Bluecrisp' or 'Magnolia'. Also, the berries of 'TO-1088' are darker than berries of 'Bluecrisp' or 'Magnolia'.

Major attractions of 'TO-1088' are its ornamental appeal, robustness, and suitability for home garden and landscape use. Preliminary studies suggest that 'TO-1088' has a small degree of self-fruitfulness and may be pollinated by rabbiteye and southern highbush varieties.

TABLE 1

2-year average ratings of some fruit and plant characteristics of 'TO-1088' and standard cultivars 'Alapaha' and 'Camellia' from 2013-2014 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2011.

| | Alapaha location | | |
|---|---|---|---|
| Berry and plant attributes | 'Alapaha' | 'Camellia' | 'TO-1088' |
| Berry size | 6.3 | 8.8 | 4.5 |
| Berry scar | 7.0 | 7.0 | 7.0 |
| Berry color | 6.8 | 8.3 | 5.5 |
| Berry firmness | 7.0 | 7.2 | 7.0 |
| Berry flavor | 7.3 | 7.5 | 7.0 |
| Cropping | 6.0 | 6.0 | 6.0 |
| Plant vigor | 8.5 | 9.5 | 7.0 |
| Date of 50% flowering | March 24 | March 13 | March 16 |
| Date of 50% ripening | June 12 | May 21 | May 28 |
| Fruit development period (days) | 80 | 69 | 73 |

TABLE 2

2-year average ratings of some fruit and plant characteristics of 'TO-1088' and standard cultivars 'Alapaha' and 'Camellia' (2013-2014) in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in 2011.

| | Griffin location | | |
|---|---|---|---|
| Berry and plant attributes | 'Alapaha' | 'Camellia' | 'TO-1088' |
| Berry size | 6.5 | 8.8 | 5.0 |
| Berry scar | 7.0 | 7.0 | 7.0 |
| Berry color | 7.0 | 8.3 | 6.0 |
| Berry firmness | 6.8 | 7.2 | 7.0 |
| Berry flavor | 7.0 | 7.2 | 7.2 |
| Cropping | 6.0 | 6.5 | 9.0 |
| Plant vigor | 7.0 | 8.5 | 7.3 |
| Date of 50% flowering | April 3 | March 27 | March 30 |
| Date of 50% ripening | June 19 | June 6 | June 23 |
| Fruit development period (days) | 77 | 71 | 85 |

BRIEF DESCRIPTION OF THE FIGURES

The accompanying photographic illustrations show typical specimens in full color of the foliage, flowering, and fruit of the new variety 'TO-1088'. The colors are as nearly true as is reasonably possible in a color representation of this type.

BOTANICAL DESCRIPTION

Figure 1:
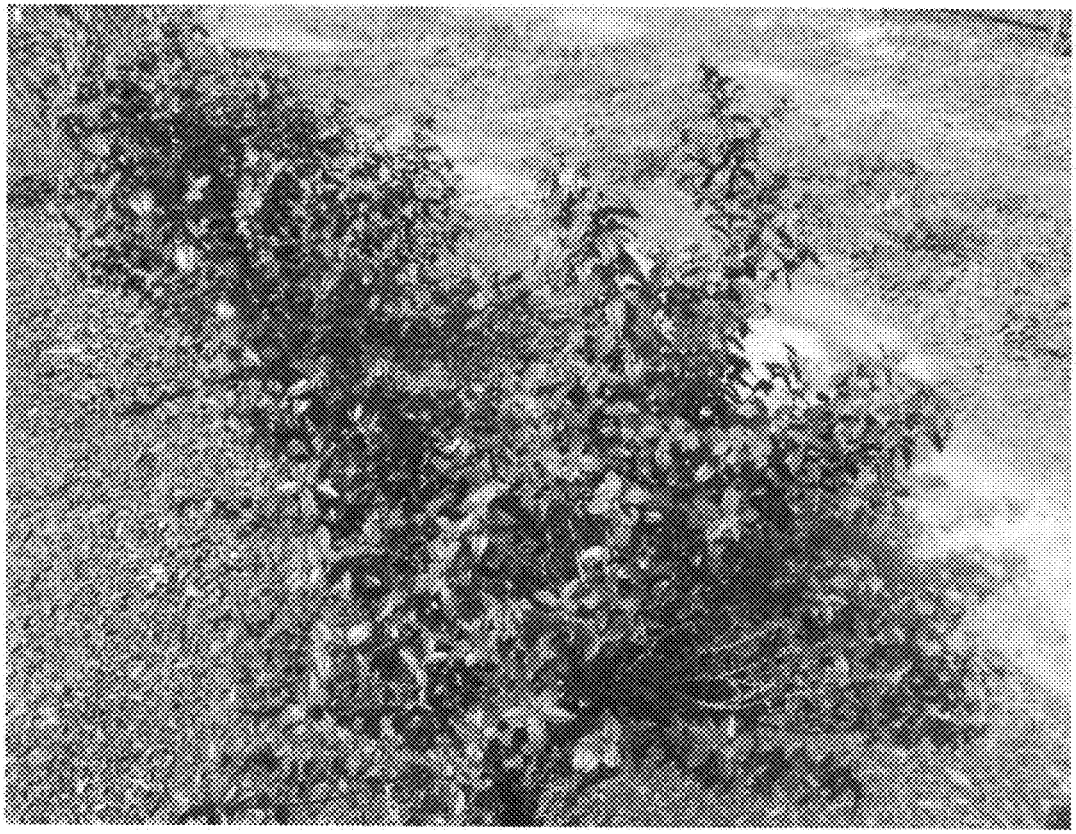
FIG. 1 is a photograph of the new variety 'TO-1088' during early flowering in Griffin, Ga.
Figure 2:
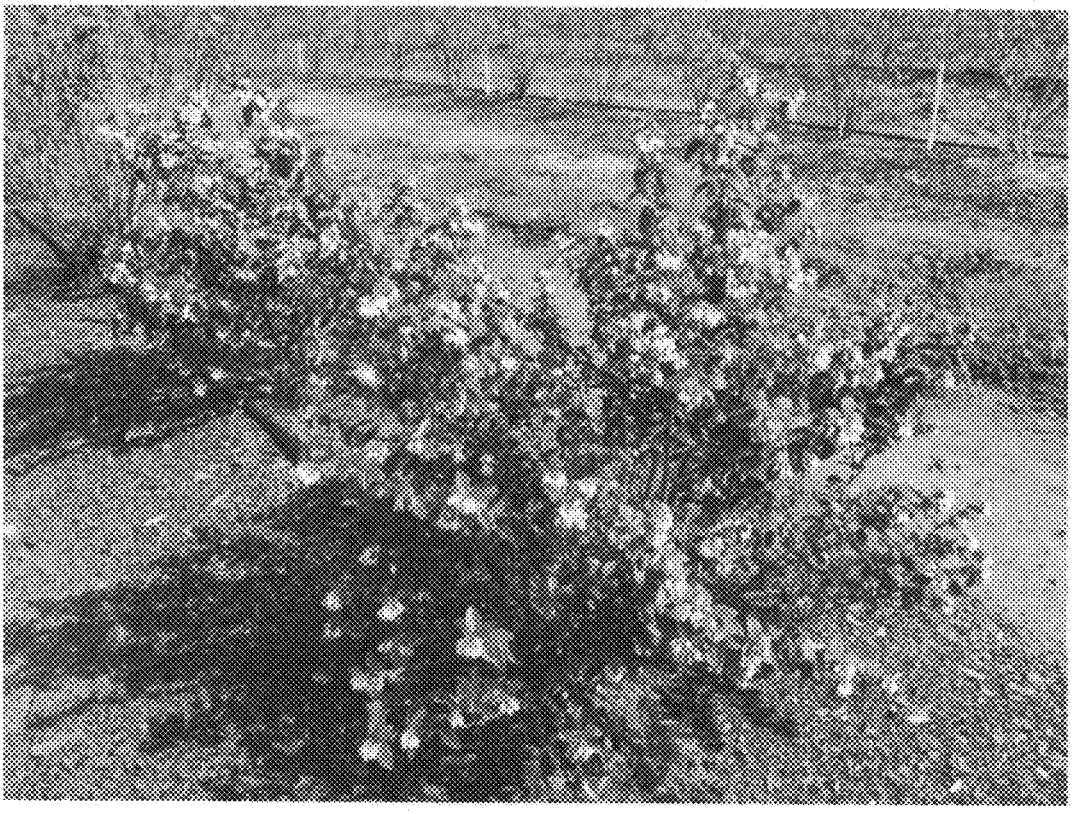
FIG. 2 is a photograph of the new variety 'TO-1088' during later flowering in Griffin, Ga.
Figure 3:
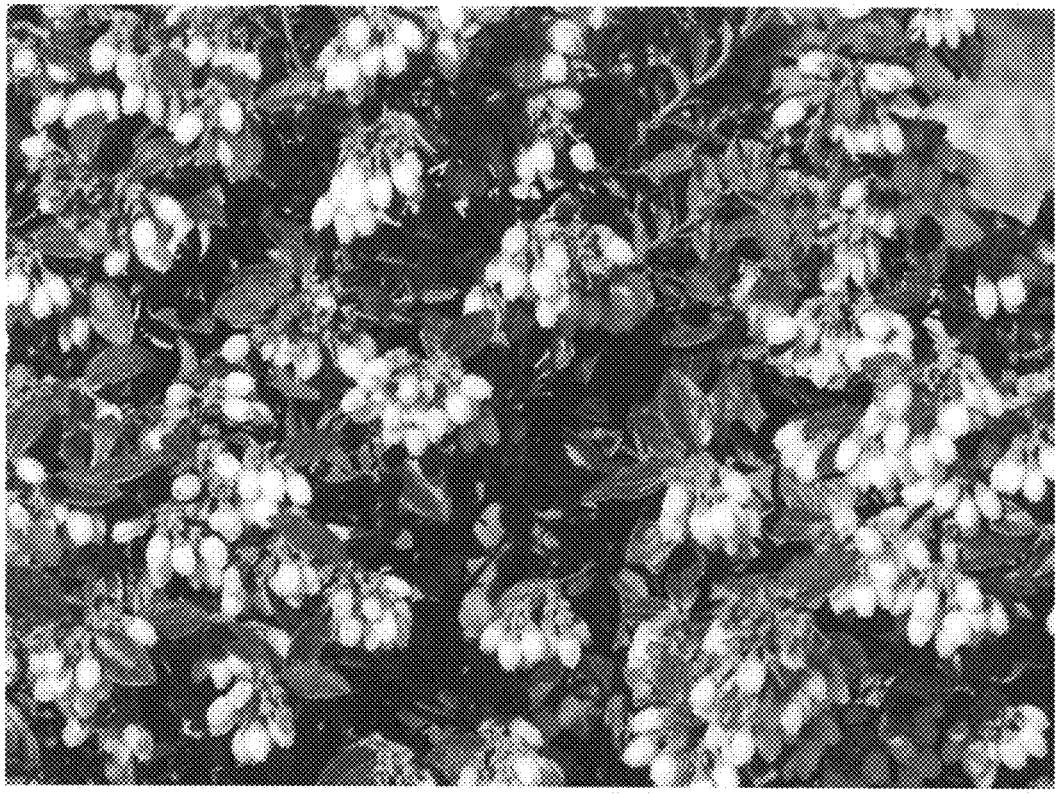
FIG. 3 is a close up photograph of the new variety 'TO-1088' during flowering in Alapaha, Ga.
Figure 4:
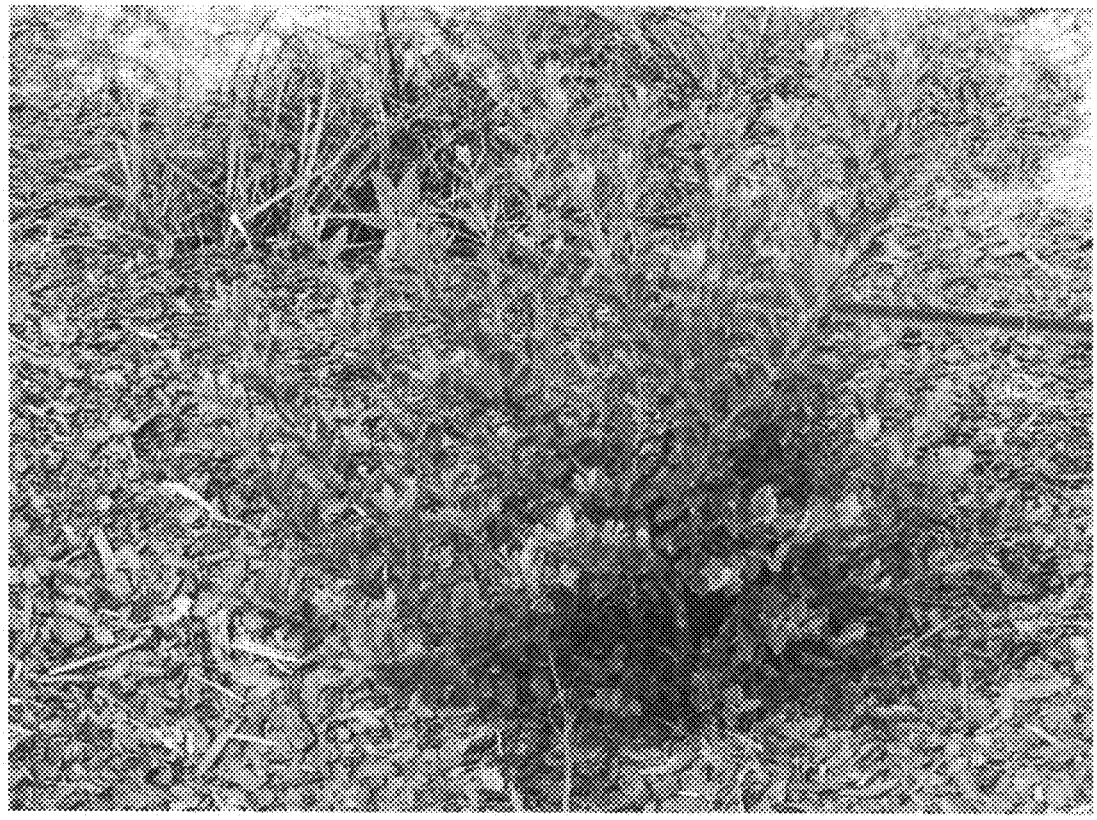
FIG. 4 is a photograph of the new variety 'TO-1088' growing at a test location in southern Georgia in early August.
Figure 5:
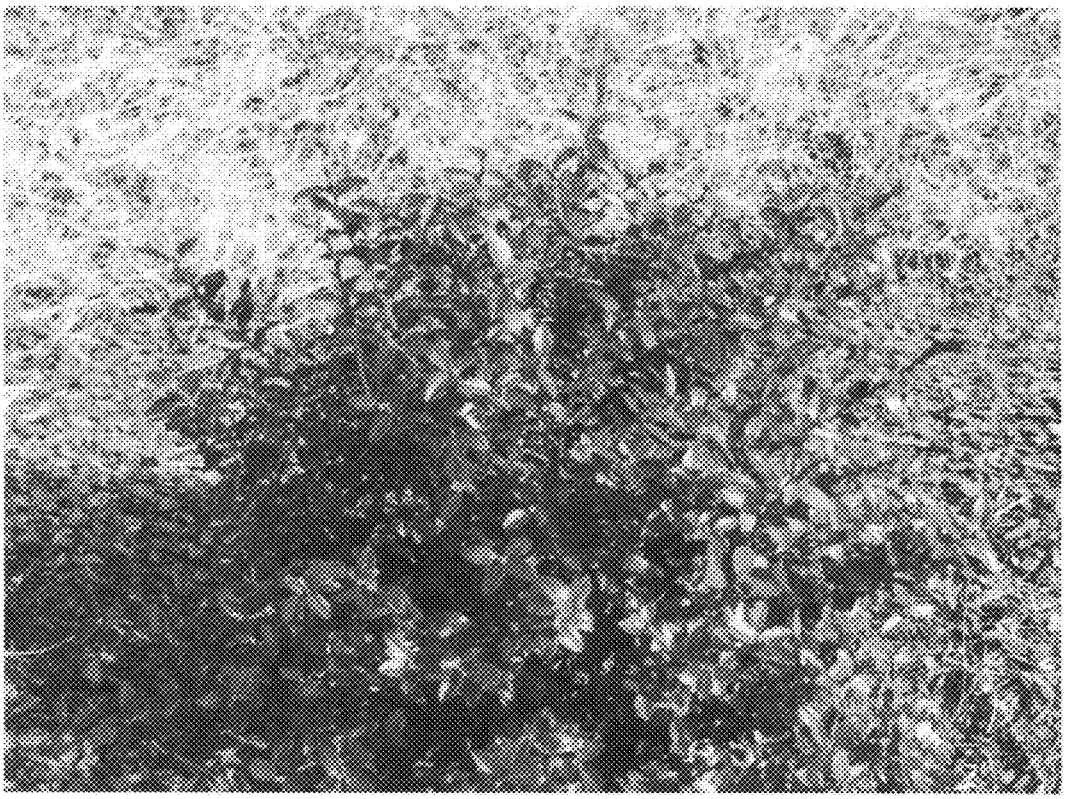
FIG. 5 is a photograph of the new variety 'TO-1088' growing at a test location in southern Georgia in early January.
Figure 6:
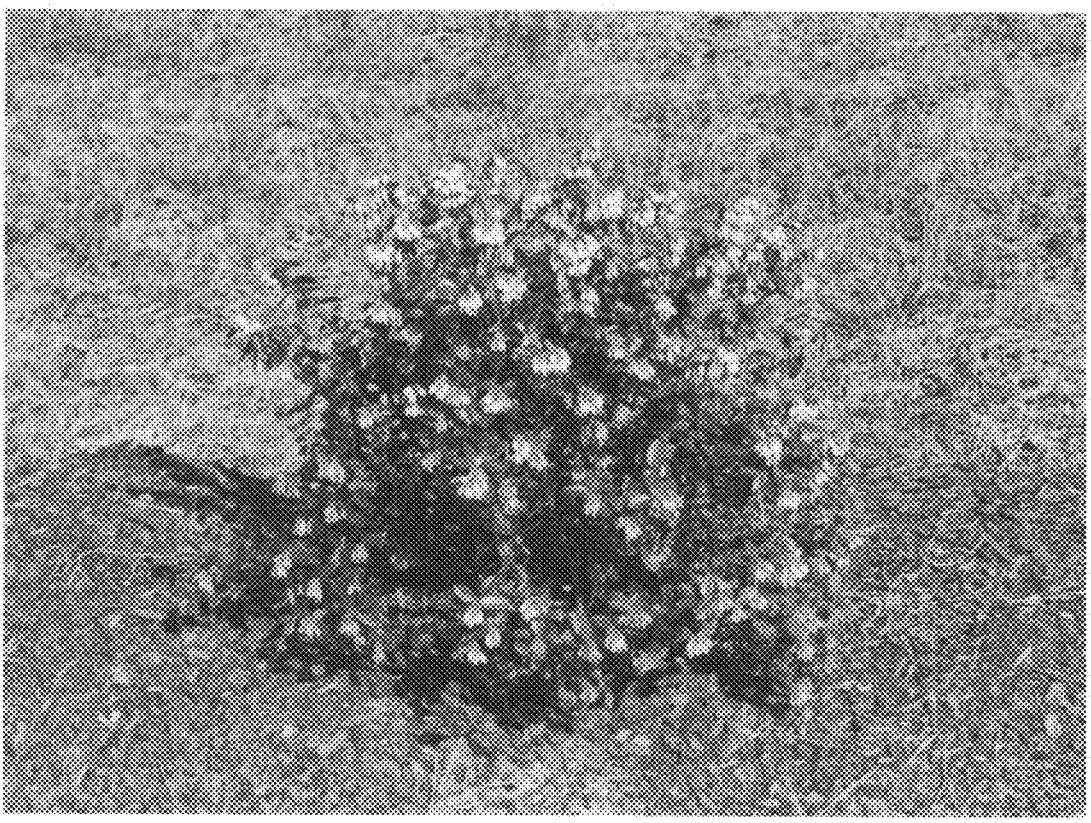
FIG. 6 is a photograph of the new variety 'TO-1088' growing at a test location in southern Georgia in late March.
Figure 7:
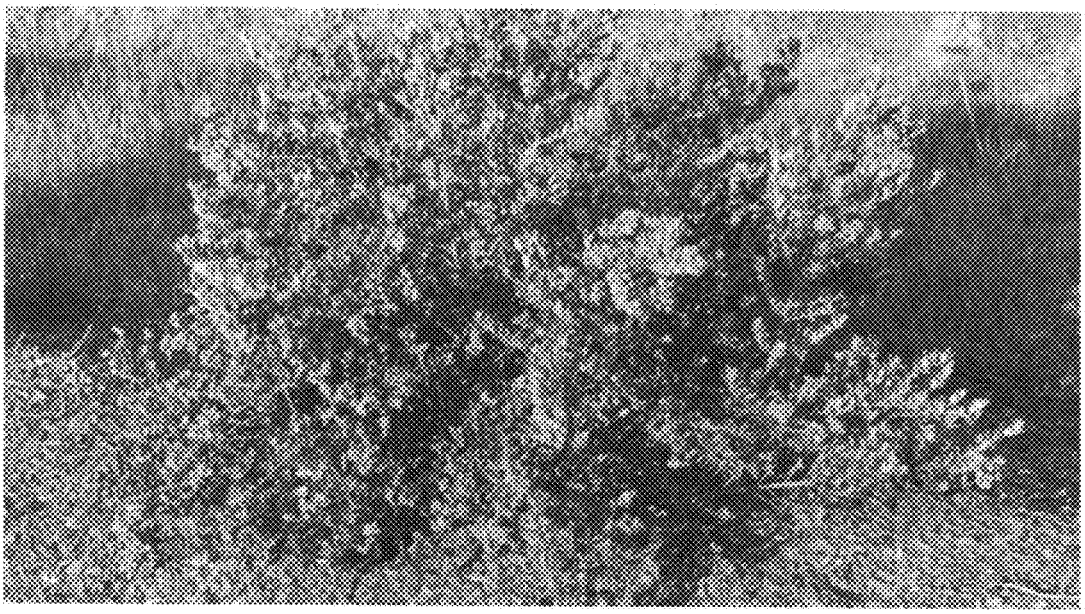
FIG. 7 is a photograph of new variety 'TO-1088' at the beginning of fruit ripening in Alapaha, Ga.
Figure 8:
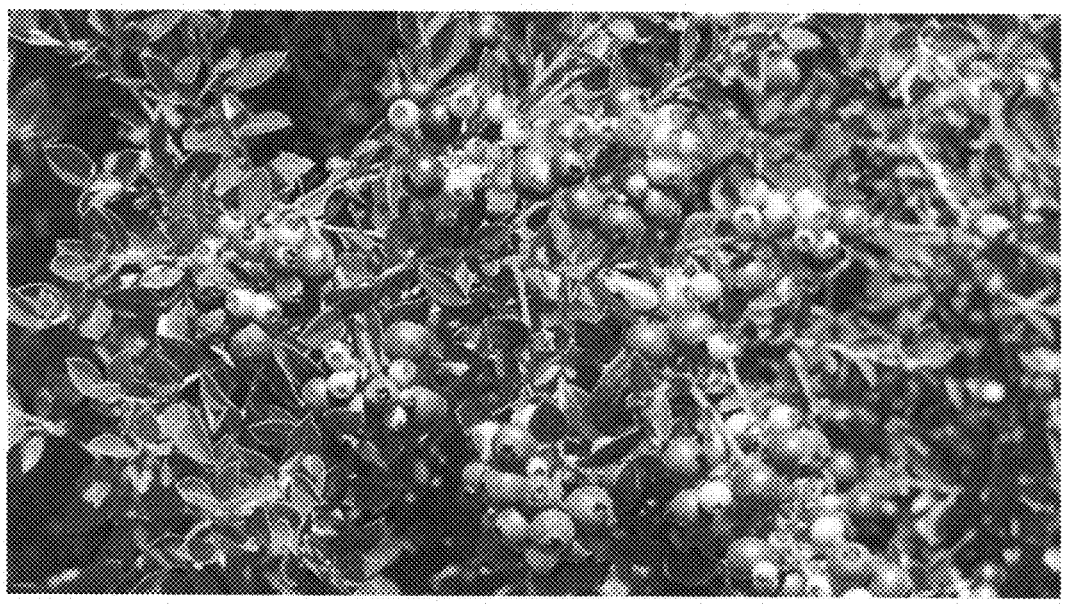
FIG. 8 is a close up photograph of the new variety 'TO-1088' fruit clusters during ripening in Alapaha, Ga.
Figure 9:
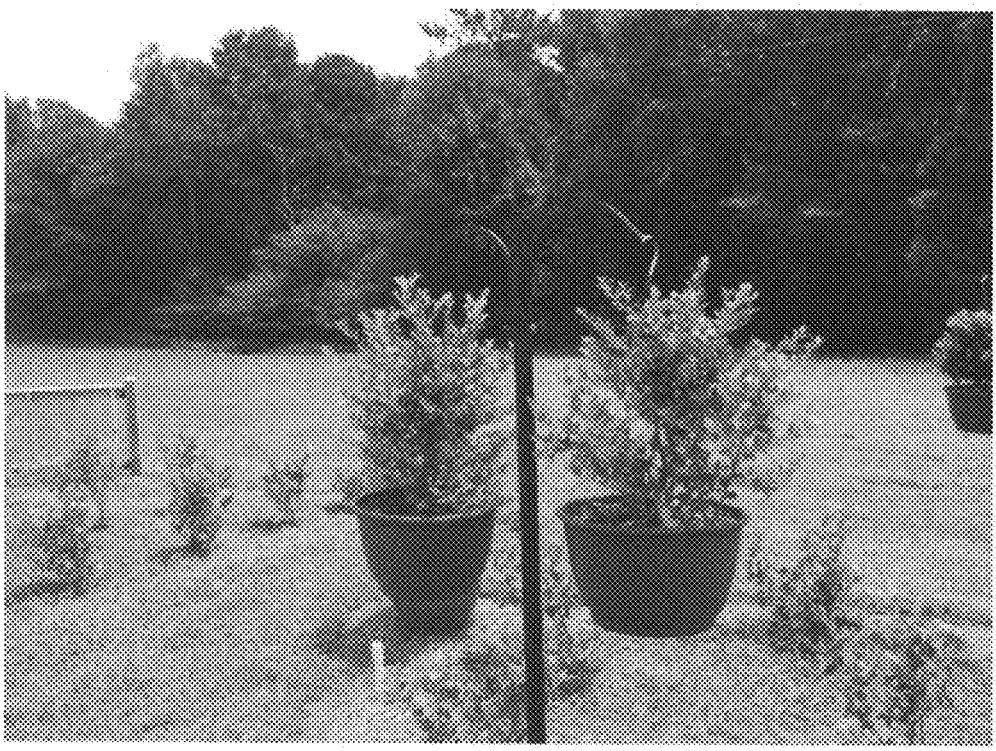
FIG. 9 is a photograph of container grown plants of the new variety 'TO-1088' in Griffin, Ga.
Figure 10:
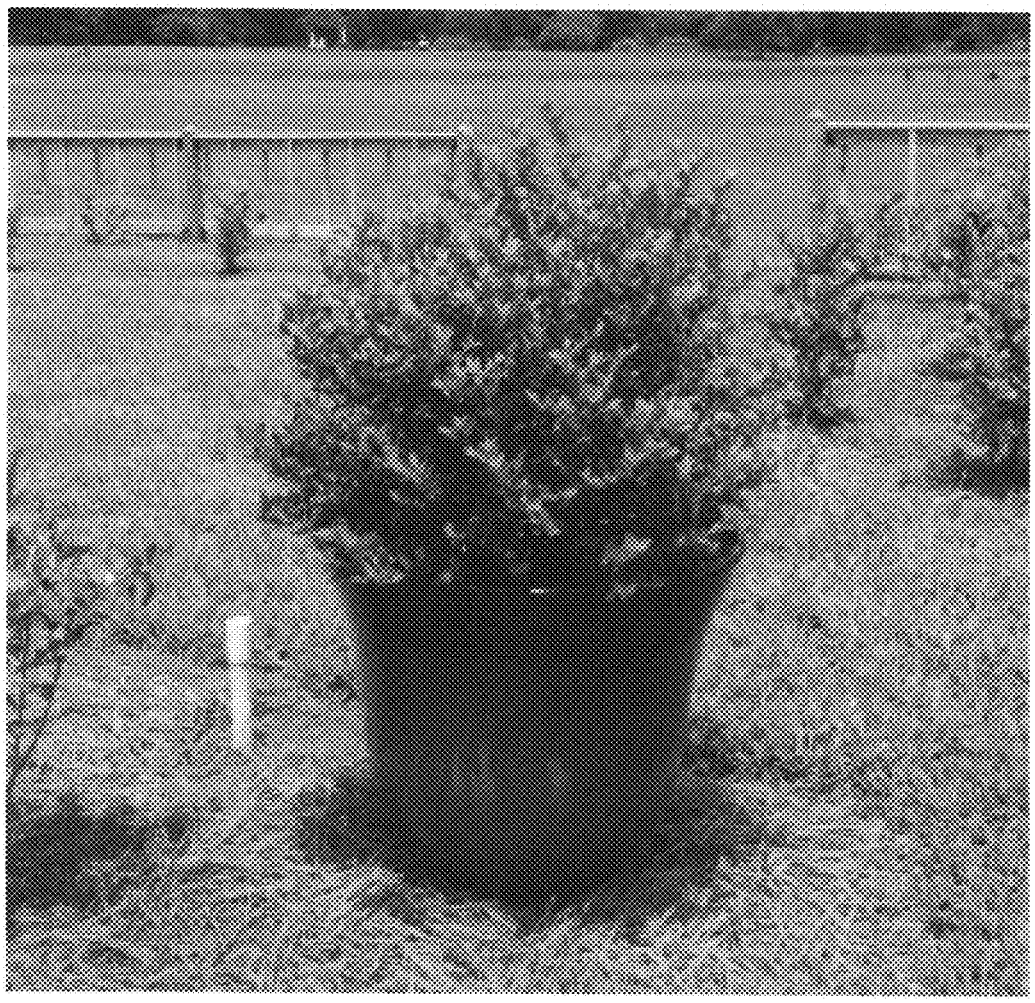
FIG. 10 is a close up photograph of another container grown plant of the new variety 'TO-1088' in Griffin, Ga.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following is a detailed description of the botanical and pomological characteristics of the new variety 'TO-1088'. Where dimensions, sizes, colors, and other characteristics are given, it is to be understood that such characteristics are approximations and averages set forth as accurately as practicable. The descriptions reported herein are largely from observations of specimen plants grown in Alapaha and Griffin, Ga., with supplemental irrigation. The observed plants were about 4 to about 6 years old.

Plant:

*Size.*—0.5 to 0.8 m tall by about 4 years of age. The plant crown, or base, is narrow, typically 10 to 20 cm in diameter. The upper portion of plant canopy reaches 0.6 to 0.9 m in diameter by 4 years.

*Growth habit.*—Spreading, dwarf with 2 to 5 main canes arising from the crown, and multiple branching of shoots (2 to 3 per cane) from those canes at 8 cm or less above the soil surface.

*Growth.*—Moderately vigorous. During mild winters plant can evergreen, holding leaves throughout the winter.

*Productivity.*—High to very high crop for dwarf ornamental blueberry, averaging 2 to 4 lbs of fruit per plant each year for plants 4 years and older grown under ideal conditions.

*Hardiness.*—Similar to other varieties such as 'Alapaha' and 'Camellia'.

*Chilling requirement.*—400-500 hours of temperatures at or below 7° C. (about 45° F.) to induce normal leafing and flowering during the spring under conventional production systems.

*Leafing.*—Plants tend to break sufficient leaf buds simultaneously with, or shortly after, anthesis.

*Canes.*—Diameter: 15 to 20 mm for base of main canes that are about 4 years old and older; 10-12 mm first major branch diameter; 5 to 10 mm in about 2 year old wood; 3 to 4 mm in current season wood. Color: Near Greyed-Green 197B for base of canes that are about 4 years old and older; near Yellow-Green 146C transitioning to Greyed-Green 197B for first major branch. Yellow-Green RHS 146C in about 2 year old wood. Green RHS 138C in current season wood.

*Fruiting wood.*—Numerous twigs 10 to 15 cm in length, with internode lengths of 5-8 mm common.

*Disease resistance.*—No exceptional disease resistance or susceptibility observed; typical for southern highbush 'Alapaha' and 'Camellia'.

Foliage:

*Leaf color.*—Healthy mature leaves. Top side: Green RHS N137D. Under side: Green RHS 138B.

*Leaf arrangement.*—Alternate, simple.

*Leaf shape.*—Elliptic.

*Leaf surface.*—Both upper and lower surfaces are glaucous.

*Leaf margins.*—Serrulate, smooth.

*Leaf venation.*—Pinnate, slightly reticulated.

*Leaf apices.*—Acute.

*Leaf bases.*—Acute.

*Leaf dimensions.*—Length: 20.0 to 25.0 mm. Width: 10.0 to 12.0 mm.

*Petioles.*—Small. Length: 1.0 to 1.5 mm. Width: 0.8 to 1.0 mm. Color: Yellow-Green RHS 145B. Relative vegetative bud burst: Medium.

Flowers:

*Date of* 50% *anthesis.*—March 16 in southeast Georgia and March 30 in middle Georgia (2 year average).

*Flower shape.*—Urceolate.

*Flower bud number.*—Very high, averaging 10 or more buds per fruiting shoot.

*Flowers per cluster.*—5 to 8 common.

*Flower fragrance.*—None.

*Corolla.*—Color: White RHS NN155D (open flower). Length: 6.5 to 7.0 mm. Width: 4.0 to 4.5 mm. Aperture width: 1.5 to 2.0 mm.

*Flower peduncle.*—Length: 10.0 to 12.0 mm; which reflects the average inflorescence size. Color: Yellow-Green RHS 145A.

*Flower pedicel.*—Length: 3.5 to 4.0 mm. Color: Green RHS 138C.

*Calyx* (*with sepals*).—Diameter: 3.5 to 4.0 mm. Color: Green RHS 138B.

*Stamen.*—Length: 5.5 to 6.0 mm. Number per flower: 10. Filament color: Yellow-Green RHS 145D.

*Style.*—Length: 7.0 to 7.5 mm. Color: Yellow-Green RHS 145B.

*Pistil.*—Length: 8.5 to 9.0 mm. Ovary color (exterior): Green RHS 138C.

*Anther.*—Length: 2.8 to 3.2 mm. Number: 10. Color: Greyed-Orange RHS 165B.

*Pollen.*—Abundance: High. Color: Yellow-Orange RHS 19C.

*Self-compatibility.*—The cultivar has a small to moderate degree of self-compatibility.

*Flower bud anthocyanin content.*—Moderate to strong during early stages of flower bud development, becoming weak at full bloom.

Fruit:

*Date of* 50% *maturity.*—May 28 in southeast Georgia and June 23 in middle Georgia (2 year average).

*Fruit development period.*—75 to 85 days.

*Fruit type.*—Fruit are on one year old shoots only.

*Berry color.*—With wax: Black RHS 202A to Black RHS 203B. With bloom: Black RHS 202A to Black RHS 203B.

*Berry surface wax abundance.*—Very low.

*Berry flesh color.*—White RHS 155C.

*Berry weight.*—First harvest: 1.0 g to 1.2 g. Second harvest: 0.6 g to 1.0 g.

*Berry size.*—Height from calyx to scar: 10.0 to 12.0 mm. Diameter: 10.0 to 12.0 mm.

*Berry shape.*—Spherical.

*Fruit stem scar.*—Small, medium-dry, with some slight tearing at harvest.

*Calyx.*—depth 1.0 to 1.5 mm; width 2.0 to 3.5 mm; sepals outward and erect when present.

*Berry firmness.*—Medium firm.

*Berry flavor and texture.*—Mildly tart; sweetening as berry matures, semi smooth texture.

*Fruit cluster density.*—Moderate

*Storage quality.*—Medium.

*Suitability for mechanical harvesting.*—Not suitable.

*Uses.*—Intended for home gardens and/or ornamental uses.

Seed:

*Seed abundance in fruit.*—Low, less than 10 fully developed seeds per berry.

*Seed color.*—Greyed-Orange RHS 165A.

*Seed dry weight.*—40.8 mg per 100 seeds.

*Seed size.*—1.0 to 2.0 mm long; 0.4 to 0.8 mm wide for fully developed seeds.

What is claimed is:

1. A new and distinct variety of dwarf hybrid blueberry plant named 'TO-1088', substantially as illustrated and described herein.

* * * * *